United States Patent [19]

Chang et al.

[11] Patent Number: 4,508,654

[45] Date of Patent: Apr. 2, 1985

[54] PREPARATION OF BIS-CARBOXY ETHYL GERMANIUM SESQUIOXIDE AND ITS PROPIONIC ACID DERIVATIVES

[75] Inventors: Ching-Te Chang, Taipei; Lian-Tze Lee, Hsinchu, both of Taiwan; Hsueh-Ling Su, St. Paul, Minn.

[73] Assignee: Industrial Technology Research Institute, Hsinchu, Taiwan

[21] Appl. No.: 344,377

[22] Filed: Feb. 1, 1982

[51] Int. Cl.$^3$ .............................................. C07F 7/30
[52] U.S. Cl. .............................................. 260/429 R
[58] Field of Search ................................... 260/429 R

[56] References Cited

U.S. PATENT DOCUMENTS

| | | | |
|---|---|---|---|
| 3,689,516 | 9/1972 | Asai et al. | 260/429 R |
| 3,793,455 | 2/1974 | Asai et al. | 424/287 |
| 3,812,167 | 5/1974 | Pahk | 260/429 R |
| 4,066,678 | 3/1978 | Sato et al. | 260/429 R |
| 4,271,084 | 6/1981 | Ishikawa et al. | 260/429 R |

OTHER PUBLICATIONS

Chemical Abstracts 46 7925(b) (1952).

Primary Examiner—Helen M. S. Sneed
Attorney, Agent, or Firm—Bert J. Lewen

[57] ABSTRACT

Reaction mixture of germanium dioxide and hypophosphorous acid or its salts in hydrochloric acid is extracted with organic solvent. This resultant is then reacted with acrylic acid or its derivatives, and further hydrolyzed to provide bis-carboxy ethyl germanium sesquioxide or its propionic acid derivatives.

11 Claims, No Drawings

PREPARATION OF BIS-CARBOXY ETHYL GERMANIUM SESQUIOXIDE AND ITS PROPIONIC ACID DERIVATIVES

This invention relates to a method for the preparation of bis-carboxy ethyl germanium sesquioxide and its propionic acid derivatives.

Germanium is a metallic element in the carbon family. It releases its outer electron when influenced by certain exterior conditions. This property is utilized by the electronic industry in the well known germanium transistors and diodes.

By the same token, when an organo germanium compound is surrounded by sufficient material capable of abstracting electrons, the germanium atom will release its outer electron, and thus provide a positively charged nucleus. An organo germanium compound of this kind can be used to modify the electric potential of abnormal cells and consequently to inhibit their activities.

Based upon the above phenomenon, K. Asai, et al have found out that a fatty acid (or its derivative) with a terminal germano sesquioxide possesses the following functions:

(1) Ehrich ascites tumour growth inhibition (U.S. Pat. No. 3,689,516, K. Asai, Sept. 5, 1972).

(2) Curing and life prolongation effect on rat ascites hepatoma AH44 and AH66 and on ACI rats BC47 tumour.

(3) Hypertension (high blood pressure) treatment (U.S. Pat. No. 3,793,455, K. Asai et al, Feb. 19, 1974).

(4) Inhibition of amyloidosis occurrence.

(5) Treating infections caused by viral cells and protozoa.

(6) Plant growth rate acceleration.

(7) Treating various diseases in clinical tests.

In the prior art, this class of compounds is prepared by the following scheme (U.S. Pat. Nos. 3,689,516 and 3,793,455; and Japanese Pat. No. 46-2498, Japan Gaishi, K.K., Jan. 21, 1974);

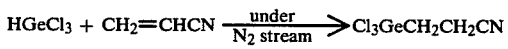

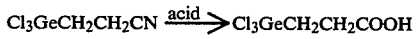

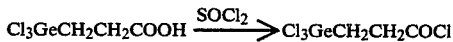

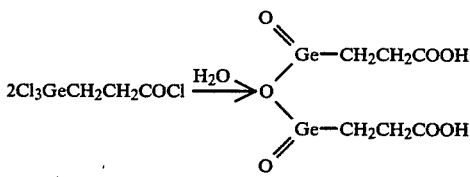

or

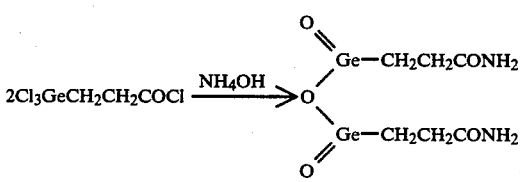

or

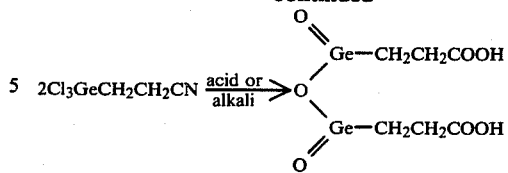

or

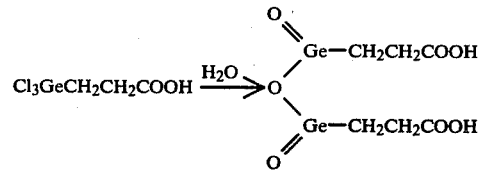

In all these processes, germanium chloroform, $HGeCl_3$, is employed as the starting germanium material; it is usually obtained from germanous compounds as follows:

(a) $GeS + HCl \rightarrow HGeCl_3$ (b) $Ge(OH)_2 + HCl \rightarrow HGeCl_3$ (c) $GeCl_2 + HCl \rightarrow HGeCl_3$ It is known that germanous compounds are unstable in nature, therefore difficult to handle and hard to purchase.

Ung Soo Pahk has suggested the following method as shown in U.S. Pat. No. 3,812,167, May 21, 1974:

$GeO_2 + HCl \rightarrow GeCl_4$ $GeCl_4 + NaH_2PO_4 \rightarrow HGeCl_3$ $HGeCl_3 + 2NH_4OH \rightarrow Ge(OH)_2$ $Ge(OH)_2 + HCl \rightarrow HGeCl_3$ $HGeCl_3 CH_2=CHCN \rightarrow Cl_3GeCH_2CH_2CN$

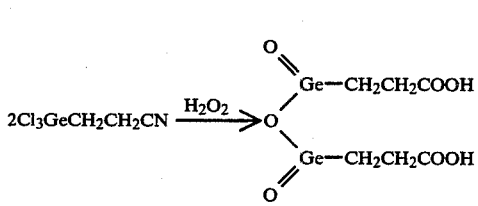

The foregoing process involves the conversion of germanium dioxide in hydrochloric acid to germanium tetrachloride, followed by reaction with monobasic sodium phosphate to give a germanium chloroform ($HGeCl_3$) mixture. In order to isolate $HGeCl_3$ from this mixture, ammonia water is used to form a germanous hydroxide precipitate. After separation, this precipitate is dissolved in hydrochloric acid and again converted to germanium chloroform. The latter is then reacted with acrylonitrile to provide trichloro germanium acrylonitrile, which upon hydrolysis with hydrogen peroxide yields bis-beta-carboxyl ethyl germanium sesquioxide.

An attempt to repeat this process has regrettably proven it to be inoperative due to the fact that the monobasic sodium phosphate has no reducing potency.

It is accordingly an object of the present invention to overcome the defects of the prior art methods while still using germanium dioxide, a commonly and easily available starting material.

Thus, referring to the equations below, in the process of the present invention germanium doxide (I) is reduced by reacting with hypophosphorous acid or hypophosphite in the presence of hydrochloric acid. The resultant aqueous solution is extracted by organic solvent (e.g. alcohol, ketone, organic ester, ether or chlorinated solvent incompatible with water). This crude germanium phosphite mixture (II) reacts with acid or its derivatives (III) at room temperature or in an ice bath (lower temperature) or in a water bath (elevated temperature) to produce a solution of crude organo germanium chlorophosphite compound (IV) in organic solvent. After evaporation of organic solvent, the residue is hydrolyzed to give the germanium sesquioxide compound V.

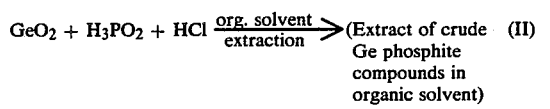

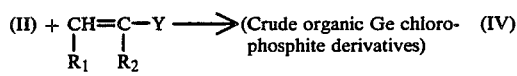

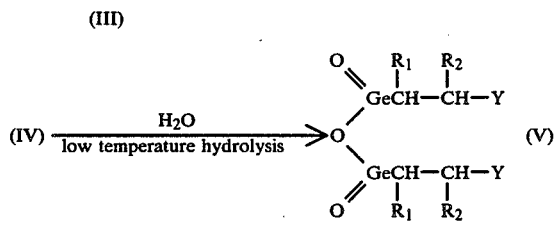

where $R_1$ and $R_2$ are the same or different and are hydrogen or lower alkyl, and Y is COOH, COOR (R being lower alkyl), $CONH_2$ or CN.

When Y is $CONH_2$ or CN, the product (V) may be hydrolyzed as follows to give the acid derivative (VI):

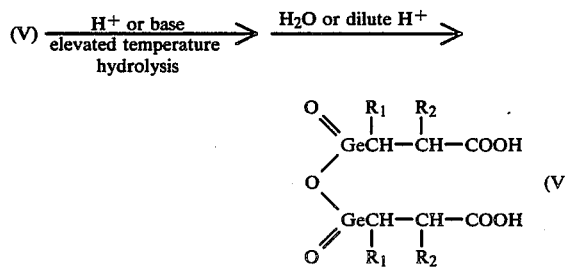

where $R_1$ and $R_2$ are as previously defined.

The unpurified organic germanium derivatives (IV) indicated in the brackets above are undefined chlorophosphite compounds. For example, when Y is $CONH_2$, the isolated intermediate (IV) is a white solid, showing characteristic IR absorptions at 2400 cm$^{-1}$ (P—H stretching), 1185 cm$^{-1}$ (P=O strenching), 1010 cm$^{-1}$ (P—O stretching), 810 cm$^{-1}$ (Ge—O stretching) and 855 cm$^{-1}$ (Ge—Cl stretching). These crude chlorophosphite intermediates are mostly unstable to other nucleophiles. In the process of the invention they receive no separation or purification yet surprisingly they can be used for the preparation of final products of pure organic germanium sesquioxide and its propionic acid derivatives.

The invention may accordingly be described as a method of making a bis organic germanium sesquioxide compound of the following formula (V):

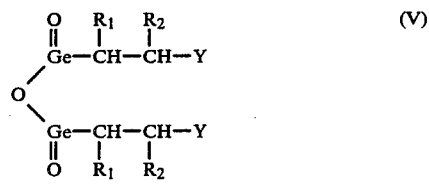

where $R_1$ and $R_2$ are hydrogen or lower alkyl (e.g., $C_1$-$C_3$ alkyl) and Y is COOH, COOR (where R is lower alkyl), $CONH_2$ or CN, involving the steps of:

(a) contacting germanium dioxide with hypophosphorous acid or a salt thereof in the presence of hydrochloric acid in an aqueous medium whereby the germanium dioxide undergoes reduction to form germanous phosphite compounds;

(b) extracting the aqueous solution formed in step (a) with an organic solvent incompatible with water;

(c) contacting the solution of germanous phosphite compounds in organic solvent obtained from step (b) with an acrylic compound of the following formula (III):

where $R_1$, $R_2$ and Y are as previously defined to form organo germanyl chlorophosphite derivatives of (III);

(d) evaporating the organic solvent from the solution resulting from step (c); and (e) contacting the organo germanyl chlorophosphite product of step (d) with water to hydrolyze the organo germanium derivatives therein whereby a bis organo germanium sesquioxide compound of said formula (V) is formed.

In one aspect, the invention is directed to such a process in which (V) is a compound wherein Y is $CONH_2$ or CN and the product (V) of step (e) is further hydrolyzed with cencentrated mineral acid or base at elevated temperature to form an acid compound (VI) according to the equation:

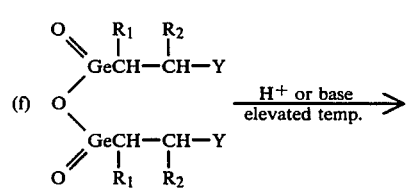

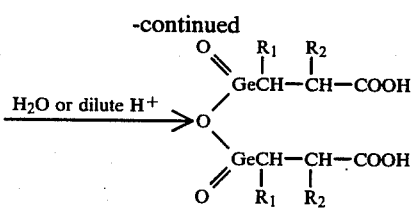

(VI)

where $R_1$ and $R_2$ are hydrogen or lower alkyl and Y is $CONH_2$ or CN.

Step (a) of the process of the invention is suitably carried out at moderately elevated temperatures, e.g., 50° C. or less to 95° C. or more (such as reflux temperature), preferably 80°–95° C. The extraction step (b) requires no critical temperature but is preferably carried out below room temperature (e.g., ice bath temperature). Examples of suitable solvents are butanol, methyl isobutyl ketone, ethyl acetate, ethyl ether, trichloroethane, etc. Step (c) is most suitably carried out at a moderate temperature, e.g., below 50° C., say at room temperature or ice bath temperature. In the hydrolysis step (e) ordinarily a low temperature (e.g., below 50° C., say at room temperature down to ice bath temperature for example) is ordinarily employed; however in converting a product (V) wherein Y is $CONH_2$ or CN to an acid product (step f), more drastic conditions (strong acid or base, elevated temperature of, e.g., 80°–100° C. or reflux temperature) are more suitable.

The following examples will serve to illustrate the practice of the invention in more detail.

EXAMPLE 1

Preparation of bis-beta-carboxy ethyl germanium sesquioxide

A. A solution of 2 g of germanium dioxide and 10 g of sodium hypophosphite in 20 ml of water and 20 ml of concentrated hydrochloric acid is placed in 100-ml, 3-necked flask. Heat in a water bath (80°–95° C.) with stirring for 4 hours, then allow it to cool. Extract this solution with 10 ml of ethyl acetate three times. Combine the extracts, add dropwise 1.5 g of acrylic acid at room temperature or in ice bath, and stir for another 4 hours. After evaporating the ethyl acetate under reduced pressure, add 20 ml of distilled water and again stir for 4 hours at room temperature or in the ice bath. Collect the crystals formed by filtration, wash with water and acetone successively. After drying, 2.5 g of the title compound is obtained, m.p. above 300° C.

Elemental analysis of Ge—Calculated: 42.6%; found 41.8%.

IR spectrum of the product shows absorption at 3300–2800, 1690, 1410, 1240 $cm^{-1}$, characteristic of COOH; and 900 and 800 $cm^{-1}$, characteristic of germanium sesquioxide. The spectrum is identical with the IR spectrum reported in Asai's book "Organic Germanium—A Medical Godsend", Japanese edition, and also agrees with those of marketed samples available from Asai Clinic.

The NMR spectrum ($D_2O$, NaOD) shows triplet peaks at 1.6 and 2.5 ppm with the same proton numbers.

B. Place 2 g of germanium dioxide in a 100-ml, 3-necked flask, wet it with a little distilled water, then added 10 ml of 10N aqueous sodium hydroxide solution. The resultant mixture is warmed up to dissolve the germanium dioxide. After cooling, add 6N hydrochloric acid to neutralize the solution and continue the addition of concentrated hydrochloric acid until the whole mixture reaches a concentration of 3N in HCl. A solution of 10 g of sodium hypophosphite in 10 ml of water is then added and the mixture is heated at reflux for 4 hours. Allow the reaction mixture to cool and extract it with 20 ml portions of ethyl ether three times. Add 2 ml of acrylic acid to the combined ether extracts in a methanol-ice bath, then stir it at room temperature for 3 hours. Evaporate the ether from the mixture, add 10 ml of distilled water to take up the residue and stir for another 4 hours. Filter the crystals formed to obtain 2.47 g (76%) of the title compound.

Substitute the said sodium hypophosphite with 50% hypophosphorous acid to give the same results. Other suitable organic solvents used in place of ethyl acetate include ethyl ether, butyl ether, butyl acetate, amyl acetate, n-butyl alcohol, or methyl isobutyl ketone. They all can provide a similar product, only in some cases the extraction rate of the solvent is not so high. Therefore the yield varies between 8 and 78%.

EXAMPLE 2

Preparation of bis-beta-carbamoyl ethyl germanium sesquioxide 2 g of germanium dioxide is reduced and extracted as in Example 1. Add 1.6 g of acrylamide to the organic extracts at room temperature and stir for 4 hours. Evaporate the organic solvent under reduced pressure. Use ammonia water to adjust the pH of the residual solution to slightly alkaline. Continue the agitation until crystals separate out. Filter the crystallized product, wash successively with water and acetone. After drying, 2.5 g of the title compound is obtained.

IR spectrum of the product shows absorption at 3400, 3200, 1660 $cm^{-1}$, characteristic of $CONH_2$; and 900, $800^{-1}$, characteristic of germanium sesquioxide.

The NMR spectrum ($D_2O$, DCl) shows triplet peaks at 1.6 and 2.5 ppm with the same proton numbers.

The acyl amido compound when hydrolyzed in the presence of strong acid or base gives the same bis-beta-carboxy ethyl germanium sesquioxide as in Example 1.

EXAMPLE 3

Preparation of bis-beta-carboxy-beta-methyl ethyl germanium sesquioxide

Treat 2 g of germanium dioxide exactly as in Example 1, but use methacrylic acid in place of acrylic acid. The reaction product is 2.3 g of the title compound.

IR spectrum of the product shows absorption at 3450, 3300–2800, 1700, 1410, 1240 $cm^{-1}$, characteristic of COOH; and 880, 800 $cm^{-1}$, characteristic of germanium sesquioxide.

NMR spectrum ($D_2O$, NaOD) shows 1.2 ppm (d,3H), 1.6 ppm(q,2H) and 2.8 ppm(m,1H).

EXAMPLE 4

Preparation of bis-beta-cyanoethyl germanium sesquioxide 2 g of germanium dioxide is reduced and extracted as in Example 1. Add 1.2 g of acrylonitrile and stir for 24 hours. Remove the ethyl acetate under reduced pressure. Extract the residue with chloroform and remove the chloroform by evaporation. Add 20 ml of water to the clear liquid thus obtained and stir for 4 hours. Filter to obtain 1.2 g of white precipitate. The IR spectrum has 2215 $cm^{-1}$ absorption for CN and 885, 790 $cm^{-1}$ absorption for germanium sesquioxide.

Treat this precipitate with 5 ml of concentrated hydrochloric acid. Heat at reflux for 4 hours and then remove most of the hydrochloric acid by evaporation. Add 20 ml of distilled water and allow to crystallize. Filter off the insoluble crystals and wash with water and acetone. After drying, 0.8 g of bis-beta-carboxy-ethyl germanium sesquioxide is obtained. The IR spectrum is the same as in Example 1.

EXAMPLE 5

Preparation of bis-beta-carbomethoxy-ethyl germanium sesquioxide

Following the procedure of Example 1, using methyl acrylate in place of acrylic acid will give the title compound. The IR spectrum is characterized by absorptions at 1730 cm$^{-1}$ for the ester, and 880, 800 cm$^{-1}$ for germanium sesquioxide. [The title compound is further hydrolyzed with 20 ml of water at reflux for 3 hours. After cooling, collect the crystalline product and wash with water and acetone. After drying, 2 g of white crystal is obtained. The IR spectrum of this product is the same as that in Example 1.]

EXAMPLE 6

Preparation of bis-beta-carboxy-alpha-methyl ethyl germanium sesquioxide

Following the procedure of Example 1, using crotonic acid in place of acrylic acid will yield 1.5 g of the title compound.

The IR spectrum shows absorption at 3300–2500, 1695, 1410 1250 cm$^{-1}$ for COOH, and 900, 790 cm$^{-1}$ for germanium sesquioxide.

What is claimed is:

1. A method of making a bis organic germanium sesquioxide compound of the following formula: (V):

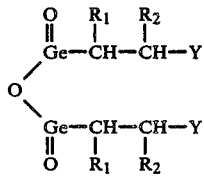

where $R_1$ and $R_2$ are hydrogen or lower alkyl and Y is COOH, COOR (where R is lower alkyl), CONH$_2$ or CN, comprising in combination the steps of:
   (a) reducing germanium dioxide with hypophosphorous acid or its salt in an aqueous medium in the presence of hydrochloric acid in a concentration sufficient to form germanous phosphite;
   (b) extracting the aqueous solution formed in step (a) with an organic solvent incompatible with water;
   (c) reacting the germanous phosphite in the solution obtained from step (b) in an organic solvent with an acrylic compound of the following formula (III):

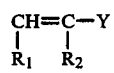

where $R_1$, $R_2$ and Y are as previously defined to form organo germanyl chlorophosphite derivatives of (III):
   (d) evaporating the organic solvent from the solution resulting from step (c); and
   (e) hydrolyzing the organo-germanium derivatives in the product of step (d) with water to form a bis organo germanium sesquioxide compound of said formula (V).

2. A method as in claim 1 in which (V) is a compound wherein Y is CONH$_2$ or CN and the compound (V) is further hydrolyzed with concentrated mineral acid or base at elevated temperature to form a compound (VI) of the formula:

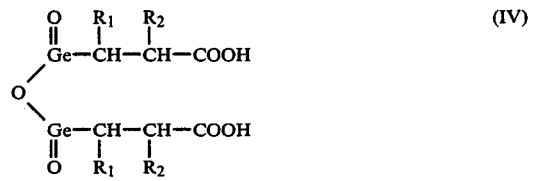

where $R_1$ and $R_2$ are hydrogen or lower alkyl.

3. A method as in claims 1 or 2 in which the reagent with which germanium dioxide is contacted in step (a) is hypophosphorous acid.

4. A method as in claims 1 or 2 in which the reagent with which germanium dioxide is contacted in step (a) is sodium hypophosphite.

5. A method as in claim 1 in which the compound (III) in step (c) is acrylic acid.

6. A method as in claims 1 or 2 in which the compound (III) in step (c) is acrylamide.

7. A method as in claim 1 in which the compound (III) in step (c) is methacrylic acid.

8. A method as in claims 1 or 2 in which the compound (III) in step (c) is acrylonitrile.

9. A method as in claim 1 in which the compound (III) in step (c) is methyl acrylate.

10. A method as in claim 1 in which the compound (III) in step (c) is crotonic acid.

11. The method of claim 1, wherein the reduction of germanium oxide in step (a) is performed in the presence of HCl in a concentration of about 3N.

* * * * *